(12) United States Patent
Pratt et al.

(10) Patent No.: US 8,469,967 B2
(45) Date of Patent: Jun. 25, 2013

(54) SURGICAL CABLE TENSIONING SYSTEM

(75) Inventors: William Ralph Pratt, Newbury Park, CA (US); Robert Arthur Bruce, Ventura, CA (US)

(73) Assignee: Kinamed, Inc., Camarillo, CA (US)

(*) Notice: Subject to any disclaimer, the term of this patent is extended or adjusted under 35 U.S.C. 154(b) by 402 days.

(21) Appl. No.: 12/792,502

(22) Filed: Jun. 2, 2010

(65) Prior Publication Data

US 2010/0305571 A1    Dec. 2, 2010

Related U.S. Application Data

(60) Provisional application No. 61/183,500, filed on Jun. 2, 2009.

(51) Int. Cl.
| | |
|---|---|
| *A61B 17/58* | (2006.01) |
| *A61B 17/60* | (2006.01) |
| *A61B 17/12* | (2006.01) |
| *A61B 17/04* | (2006.01) |
| *A61F 2/00*  | (2006.01) |

(52) U.S. Cl.
USPC .......................................... 606/103; 606/144

(58) Field of Classification Search
USPC ........... 606/74, 103, 140, 141, 139, 144–147; 140/93 B, 123.5, 101, 102.5; 81/486; 112/59, 112/156, 169; 87/61; 242/475.1; 289/17
See application file for complete search history.

(56) References Cited

U.S. PATENT DOCUMENTS

| | | | |
|---|---|---|---|
| 6,589,246 B1 | 7/2003 | Hack et al. | 606/74 |
| 6,752,810 B1* | 6/2004 | Gao et al. | 606/103 |
| 7,207,090 B2 | 4/2007 | Mattchen | 24/136 R |
| 2003/0208210 A1* | 11/2003 | Dreyfuss et al. | 606/144 |

FOREIGN PATENT DOCUMENTS

GB    2214113 A    8/1989

OTHER PUBLICATIONS

PCT Notification of the International Search Report and the Written Opinion of the International Searching Authority, Dated Oct. 13, 2010, for International Application No. PCT/US2010/001613.
"Supercable™ Iso-Elastic™ Cerclage System", Surgical Technique, Kinamed Inc., (2008).
"CL201 Installation Drawing", Clamcleat Limited, (Oct. 1998). 1 Page.

* cited by examiner

*Primary Examiner* — Kevin T Truong
*Assistant Examiner* — David Bates
(74) *Attorney, Agent, or Firm* — Koppel, Patrick, Heybl & Philpott

(57) ABSTRACT

A cable tensioning system includes a reaction frame which contains a sliding platform arranged to move linearly within the frame, and a clam-type cleat attached to the sliding platform. The cleat features one or more grooves, each of which comprises two arrays of opposing ridges that converge to form a V-shape groove adapted to receive a length of cable. The ridges of each groove are tilted relative to an axis perpendicular to the groove's longitudinal axis, such that the cable is progressively captured between the ridges of the opposing arrays as it settles into the crotch of the groove when moved in a first direction, and can be disengaged from the cleat by relaxing the axial force on the cable and moving it in the opposite direction. A linear actuator mechanism may be coupled to the sliding platform to move the platform with respect to the reaction frame.

22 Claims, 4 Drawing Sheets

SURGICAL CABLE TENSIONING SYSTEM

RELATED APPLICATIONS

This application claims the benefit of provisional patent application No. 61/183,500, filed in the U.S. Patent and Trademark Office on Jun. 2, 2009.

BACKGROUND OF THE INVENTION

1. Field of the Invention

This invention relates generally to cable tensioning systems, and more particularly to systems for tensioning surgical cables employed to hold human body tissues and/or bones in a desired relationship or position.

2. Description of the Related Art

Many products are known which serve to hold human body tissues and bones in a desired relationship or position, to aid in their healing when injured or diseased. One such product is the surgical cable, which can be wrapped around the fragments of a fractured bone, for example, such that a compressive force is applied which aids in the healing of the bone. Such a cable is described, for example, in U.S. Pat. No. 6,589,246 to Hack et al.

After the cable has been wrapped around the anatomical structures to be held, the resulting looped cable is tightened to apply a desired level of compressive force to the structures. The cable forming the loop is then locked into place with a cable retaining device such as that described in U.S. Pat. No. 7,207,090 to Mattchen.

Tightening the looped cable to apply a desired level of compressive force requires a means of tensioning the cable. Previous systems have used various types of actuated clamping jaws to grip the cables. For example, one such tensioning system, described in SuperCable™ Iso-Elastic™ Cerclage System—Surgical Technique, Kinamed Inc. (2008), employs a clamping jaw that is screwed down using a hand operated wrench. However, the swing of the wrench requires unrestricted space that may not be available when working in deep wounds; i.e., the patient's muscle and fatty tissues may crowd in around where the tensioner needs to be deployed. Such systems may also be seen as suboptimal in terms of reliability and time required to operate.

SUMMARY OF THE INVENTION

A cable tensioning system is presented which provides a simple, convenient, and reliable means of tensioning a cable, and is particularly well-suited for use in tensioning surgical cables which have been wrapped around one or more tissues and/or bones.

The present tensioning system includes a reaction frame which contains a sliding platform arranged to move linearly within the frame along a first axis, and a clam-type cleat attached to the sliding platform. The cleat features one or more grooves, each of which comprises two arrays of opposing ridges that converge to form a V-shape. Each of the V-shaped grooves has a longitudinal axis which is approximately parallel to the first axis, and is adapted to receive a length of cable such that the cable lies along an axis approximately parallel to the groove's longitudinal axis. The ridges of each groove are tilted relative to an axis perpendicular to the groove's longitudinal axis, such that the length of cable is progressively captured between the ridges of the opposing arrays as it settles into the crotch of the groove when moved in a first direction relative to the cleat, and such that the cable can be disengaged from the cleat by relaxing the axial force on the cable and moving it in the opposite direction.

A linear actuator mechanism is preferably coupled to the sliding platform and arranged to move the sliding platform with respect to the reaction frame; the mechanism can be arranged to be driven by either manual or powered means. The system may also include an anti-snag device arranged to occlude the grooves and thereby prevent the cable from being captured if desired. A threading assist device may be coupled to the reaction frame to assist in threading cables to be tensioned into the tensioning system.

These and other features, aspects, and advantages of the present invention will become better understood with reference to the following drawings, description, and claims.

DETAILED DESCRIPTION OF THE INVENTION

A cable tensioning system in accordance with the present invention provides a simple, convenient, and reliable means of tensioning a cable. A primary application of the system is to apply tension to a surgical cable or cables which have been wrapped around one or more tissues and/or bones, such that the cables apply a compressive force to the tissues to aid their healing.

Figure 1A:
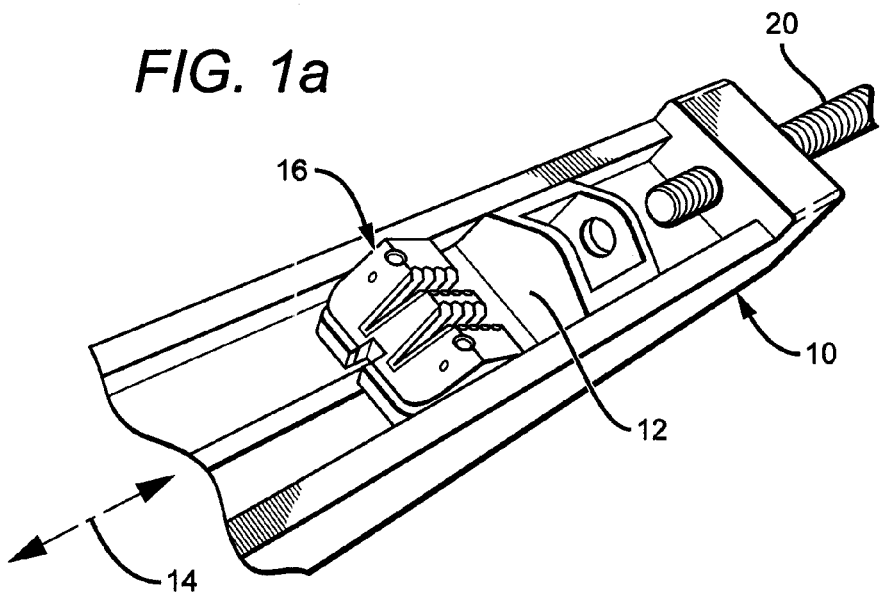
FIGS. 1a and 1b are perspective views of one possible embodiment of a surgical cable tensioning system in accordance with the present invention.
Figure 1B:
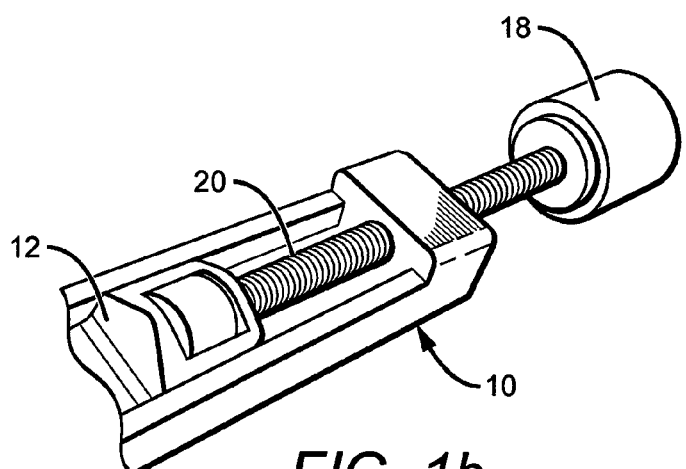

FIGS. 1a and 1b show one possible embodiment of a surgical cable tensioning system in accordance with the present invention. The system includes a reaction frame 10 which supports a sliding platform 12 which is arranged to move linearly within the frame along a first axis 14; sliding platform 12 might include rollers which track corresponding slots in the inner sidewalls of reaction frame 10 to facilitate sliding. The system also includes a clam-type cleat 16 (not visible in FIG. 1b) attached to sliding platform 12 such that it moves linearly within frame 10 along with the platform.

The system preferably also includes a linear actuator mechanism 20 which is coupled to sliding platform 12 and is arranged to move the sliding platform linearly with respect to reaction frame 10 when actuated. The linear actuator mechanism may be driven by manual or powered means. The driving means may have, for example, a rack configuration, or a screw configuration as shown in FIGS. 1a and 1b, which moves sliding platform 12 with respect to reaction frame 10 when rotated. A screw configuration may utilize a multiple-start threaded screw that results in faster actuation of the sliding platform. When a screw configuration is employed, linear actuator mechanism 20 may include a tightening knob 18 attached to the screw. The tightening knob might include a torsion spring coupled to the screw, arranged such that turning the knob deflects the spring and adjusts the tension realized in the cable. Preferably, the amount of tension realized in the cable for a given amount of deflection in the torsion spring is known.

Figure 2A:
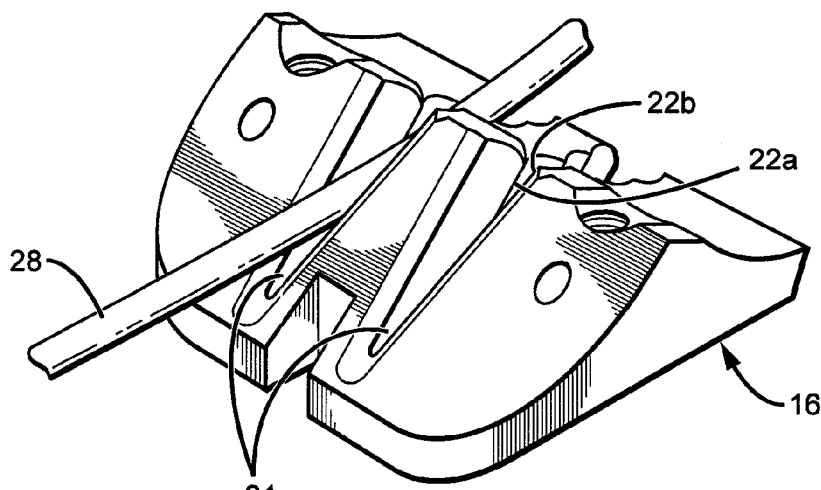
FIGS. 2a and 2b are perspective views of the clam-type cleat used with the present surgical cable tensioning system.
Figure 2B:
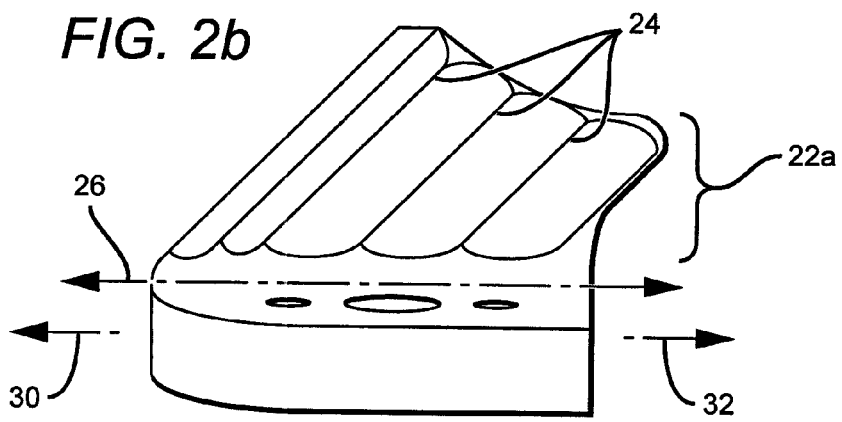

Cleat 16 is a clam-style cleat; such cleats have no moving parts and are often used in nautical applications, typically anchored in a static position, to temporarily grasp woven ropes and cables. Clam-type cleats are well-known and available from many manufacturers, such as Clamcleats Limited in Welwyn Garden City, England. As shown in FIGS. 2a (perspective view) and 2b (cutaway view), the cleat has one or more grooves 21 (two grooves are shown in FIG. 2a; one-half of one groove is shown in FIG. 2b). Each groove comprises two arrays 22a, 22b of opposing ridges 24 that converge to form a V-shape. Each of the V-shaped grooves has a longitudinal axis 26 which, when mounted to sliding platform 12, is approximately parallel to first axis 14. Each groove is adapted to receive a length of cable 28 such that, when positioned in the groove, the length of cable lies along an axis approximately parallel to the groove's longitudinal axis 26.

The opposing ridges of each groove are tilted relative to an axis perpendicular to the groove's longitudinal axis, such that the cable 28 is progressively captured between the ridges of the opposing arrays as it settles into the crotch of the groove when moved in a first direction 30 relative to the cleat 16. The cable is ultimately directed to an intense pinch point, at which the cable can resist great axial force without slipping within the cleat and without breakage or fracture of the cable. The cable is disengaged from the cleat by relaxing the axial force on the cable and moving the cable in the direction opposite the first direction (32), because in that direction the ridges are diverging and the cable is immediately directed away from the pinch point. The number and configuration of the ridges are important in consideration of the surgical cable tensioning system, because the pinching effect must be controlled and shared in several locations along the cable in order to develop the desired tensile load without slippage or breakage. The cleat can be made from almost anything rigid, but metal, high performance plastic, or ceramic would be the most likely candidates for surgical use. In a preferred embodiment, the clam-type cleat has two V-shaped grooves as described above, and is designed to receive and capture polymer surgical cable.

Although the cleat itself has no moving parts, the configuration of the ridges is critical to the success of the system, which is preferably designed specifically for use with an intended cable-type such as polymer surgical cable. The phenomenon of convergence leading to an effective, yet not-overwhelming, pinch point is controlled by a concert of shapes acting in proportion to the size and composition of the cable. The groove's V-shape naturally accommodates a range of cable diameters without adjustment, with the range governed by the width of the opening at the top of the "V", and how narrow it gets at the bottom of the "V". A cleat which provides an adjustable "V"—with sides that could be moved apart or closer together to extend the range—is also contemplated.

One advantage of the present system is its ability to easily engage a cable at the site of a surgical wound, due to the V-shaped grooves of the clam-type cleat. This is important because of the elasticity of the typical surgical cable, and the need to apply load to the smallest initial cable length possible. The V-shaped grooves eliminate the need to tighten a holding mechanism as with previous designs; here, the cable is simply depressed into the grooves. Note that V-shaped grooves as described herein reliably engage the cable even when slippery due to the patient's bodily fluids and/or fat.

To make the "V" an easy visual target for engaging the cable, each leg or side of the "V" is preferably in two segments. Near the top or opening of the "V", the angle of the "V" is wider. The angle between the sides, however, preferably changes and narrows closer to the point of the "V", a feature that is critical for creating mechanical advantage in the pinching process. Too broad an angle at the point of the "V" will defeat the pinching action, so it should be under 25 degrees inclusive. The sides should not actually touch or completely converge at the point of the "V", however, because this could cut the cable or fracture its core. In other words, the pinching process should be halted at a certain point of engagement. On the other hand, if the sides are too far apart, the pinch will be insufficient to resist the high axial load that needs to be imparted to the cable for its installation without the cable slipping through the cleat. The compound angle in the "V" also allows the "V" to be shorter in height for a given amount of desired opening, thus making the overall cleat more compact. The ridges themselves must not be so sharp as to slice the cable, but still must be able to bluntly dig into it. The number of ridges on each side of the "V" may vary from one to many, but one ridge is likely to overload one location on the cable when high axial force is applied, and over four ridges is potentially redundant and lessens the compactness of the device.

The angle at which the ridges are tilted relative to the axis of the cable affects the mechanical efficiency of the pinch process, compactness of the device, and the ease with which the cable is removed from cleat. If the ridges are perpendicular to the longitudinal axis of the groove, there is little natural tendency for the cable to be directed down into the pinch point. If the ridges are tilted almost all the way over, then the groove must necessarily become stretched out and take up more room. Having the ridges tilted to an angle of 45±20 degrees with respect to the perpendicular is preferred.

In practice, once a cable which is wrapped around some tissues has been sufficiently tensioned by the present system, the cable is locked into place and the tensioning system removed. An "anti-snag" device may be employed to prevent the cables from inadvertently re-engaging with the cleat when removing the tensioning system. Such a device operates by occluding the grooves of the cleat.

Figure 3:
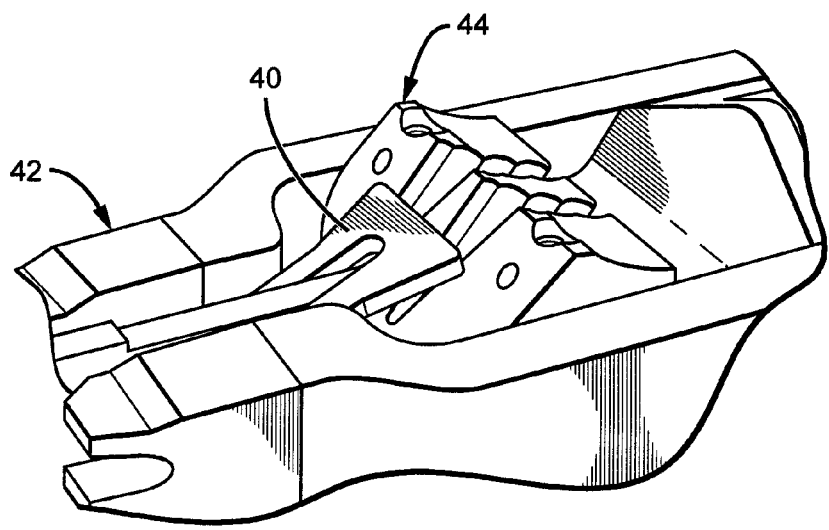
FIG. 3 is a perspective view of one possible embodiment of an anti-snag device as might be used with the present surgical cable tensioning system.

One possible anti-snag device, shown in FIG. 3, comprises a flap 40 connected to the reaction frame 42 and arranged to automatically ride up the face of the cleat 44 and occlude its grooves when the cleat is at a predetermined position with respect to the frame. Typically, flap 40 would be mounted at the end of the reaction frame nearest the point of engagement with the cable, such that the flap rides up the face of the cleat and occludes the grooves when the sliding platform is advanced completely to that end of the reaction frame.

Figure 4A:
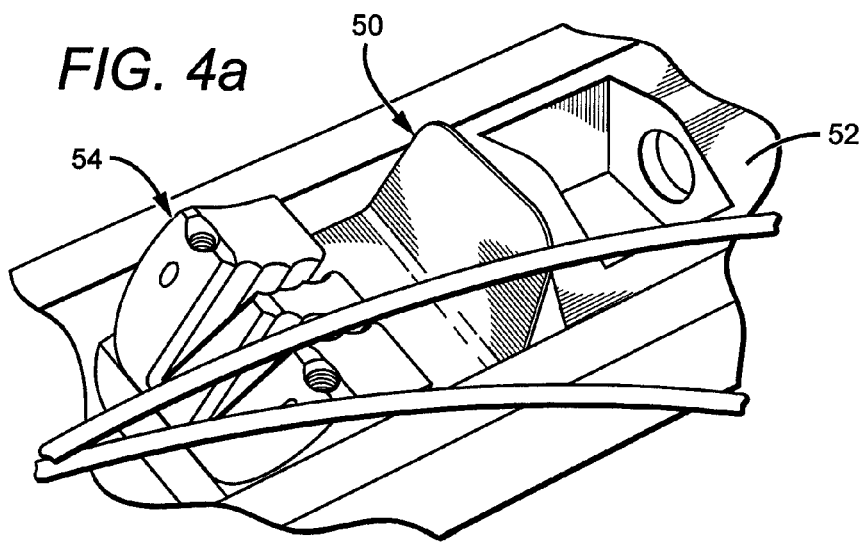
FIGS. 4a and 4b are perspective views of another embodiment of an anti-snag device as might be used with the present surgical cable tensioning system.
Figure 4B:
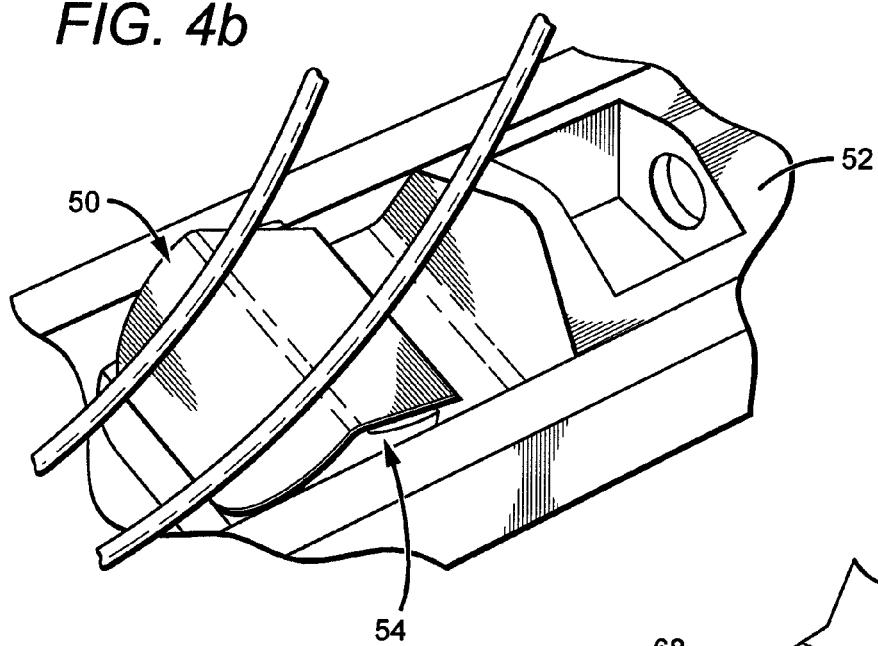

Another possible anti-snag device, which can be manually deployed to occlude the cleat grooves, is illustrated in FIGS. 4a and 4b. Here, the anti-snag device takes the form of a shield 50 which is attached to the sliding platform 52, and can be manually rotated such that the grooves of cleat 54 are unaffected (FIG. 4a) or occluded (FIG. 4b) as needed.

The advantages of using an anti-snag device are important for surgical convenience. The clam-type cleat employed in the present system is highly effective at grasping the cable, and the slightest engagement with the cable is quickly amplified when the cable is pulled relative to the cleat in the direction of convergence. After the cable has been tensioned and locked, there is a natural tendency of the cable to snag in the cleat as the tensioner is pulled away from the installation site, because that motion is again moving the cable in the direction of convergence.

Figure 5A:
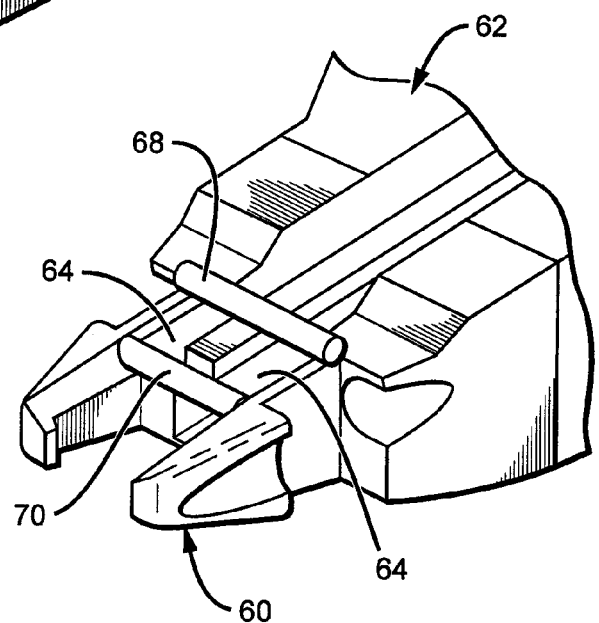
FIGS. 5a-5c are perspective views of a threading assist device as might be used with the present surgical cable tensioning system.
Figure 5B:
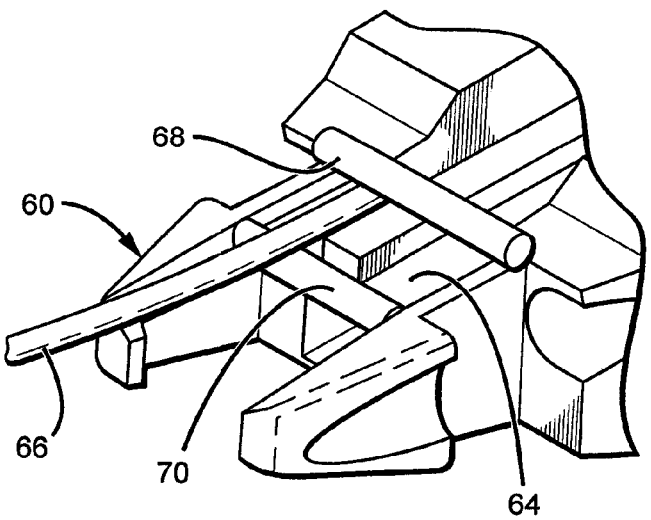
Figure 5C:
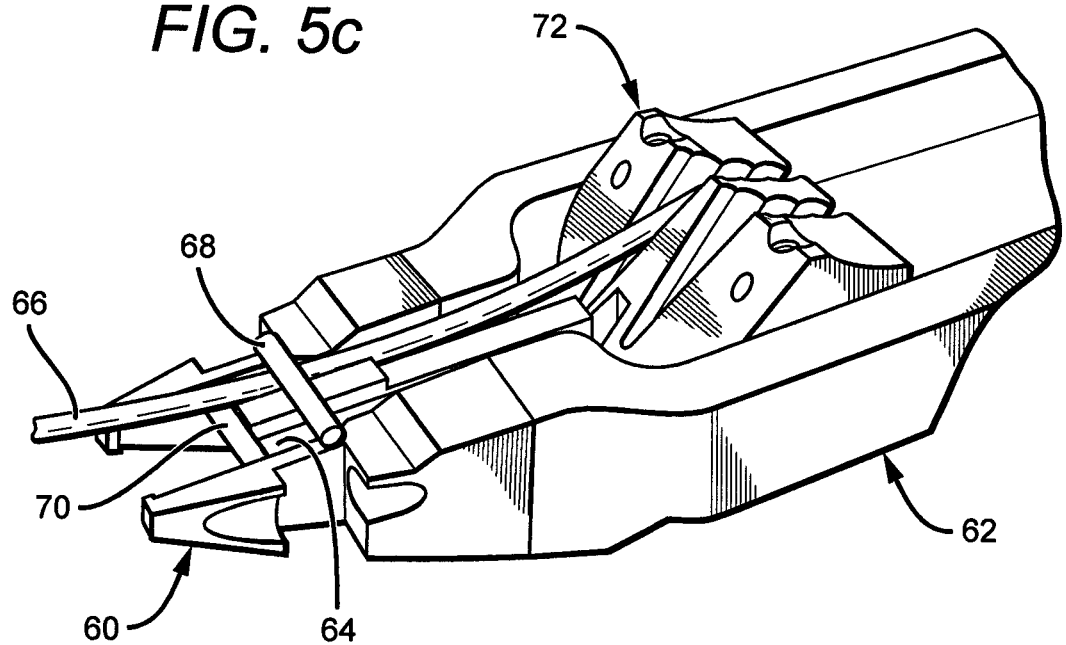

The present tensioning system may also include a threading assist device, to assist in threading the cable or cables into the cleat; one possible threading assist device is illustrated in FIGS. 5a-5c. The threading assist device 60 is coupled to the reaction frame 62, and includes at least one channel 64 (two channels are shown in FIGS. 5a-5c), each channel oriented such that its longitudinal axis is approximately parallel to first axis 14 and adapted to receive a length of cable 66. The threading assist device preferably also includes upper and lower bars 68, 70 which span the channels so as to, in concert with the sidewalls of the channels, form at least one closed loop through which a length of cable to be tensioned is threaded enroute to the grooves of the cleat 72; one closed loop is formed for each channel spanned by bars 68 and 70. The upper and lower bars are preferably staggered along the channels' longitudinal axes so as to increase the effective size of the closed loops and thereby increase the ease with which the necessary threading step may be completed. As best seen in FIG. 5c, the channels 64 serve to direct the cables into the grooves of the cleat 72.

Figure 6:
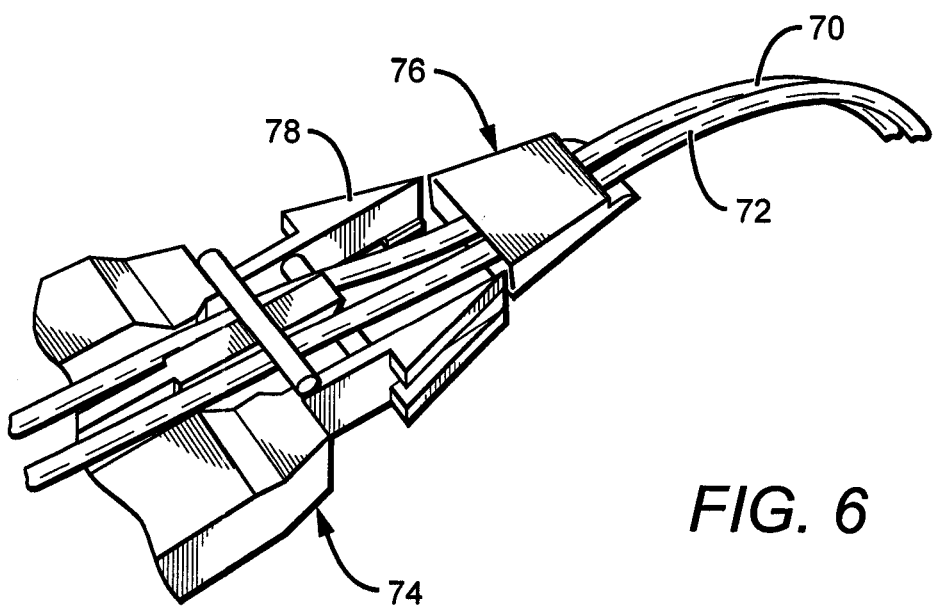
FIG. 6 is a perspective view of one possible embodiment of the present surgical cable tensioning system and a cable retaining device as they might be employed in practice.

Once the cable has been tensioned as needed, its free ends may be secured with, for example, a cable retaining or locking device through which the cable is threaded and which can be operated so as to inhibit movement of the cable with respect to the retaining device. One such possible arrangement is shown in FIG. 6, which shows cables 70 and 72 threaded through threading assist device 74 (the cleat, reaction frame and sliding platform are not shown) and a cable retaining device 76. One suitable cable retaining device is described in U.S. Pat. No. 7,207,090 to Mattchen.

The threading assist and cable retaining devices may include mating features which control the alignment and transfer of forces between the two devices when they are in contact with each other. For example, the "nosepiece" 78 of the threading assist device may have a pair of "L"-shaped projections at its tip that loosely embrace a pair of corresponding notches in the retaining device 76, with the "feet" of the "L"s butting against the opposing sides of the notches as tension is applied. In actual use, the cable is first threaded through the cable retaining device and then into the present tensioning system. Tension is then applied as needed, the retaining device is locked with a locking device such as a wedge, and the tensioning system is removed. The mating features enable an alignment between the devices which facilitates the efficient development of high tension, as well as the operation of the push rod mechanism for setting the locking wedge into place within the retaining device. The mating features are preferably arranged such that, as tension is applied, the notches guide the locking device to a pair of stops built into the "L"s.

The threading assist device is preferably configured to guide the tensioner along the cable in a sliding manner to the target mating position with the cable retaining device. Note that if the staggered bars 68, 70 are positioned too close to the tip of nosepiece 78, then the cable may be too constrained and can interfere with the nosepiece's ability to mate with the cable retaining device. Alternatively, if the bars are positioned too far away from the tip of the nosepiece, then there may not be enough constraint, such that the tip may be allowed to wander off target and fail to conveniently mate with the retaining device. The ability to easily mate with the retaining device is especially important in deep wounds were visualization is a challenge.

The present tensioning system provides a number of advantages over previous systems. For example, no moving parts are required to provide the gripping function, thus lowering production cost, improving sanitization after surgery, improving reliability and durability, and reducing the working space required to operate the tensioning system, thereby enabling the system to be more easily used in deep wounds. The time required to operate the screw as found in previous designs is eliminated in the present system, thus reducing the length of time required for surgery and providing an immediate health benefit to the patient and cost benefit to the hospital. Furthermore, since polymer cables are elastic and the cleat can be positioned closer to the engagement end of the reaction frame (i.e. deeper in the wound) because of the reduced working space requirement, the length of cable needing to be stretched is reduced and less motion is required to fully tension it—so operative time is again reduced. These time savings are multiplied in complex surgeries wherein multiple cables are used, thereby saving several minutes of costly operating room time per surgery.

As noted above, the linear actuator may utilize a multiple-start threaded screw that results in faster actuation of the sliding platform. A multiple-start threaded actuator reduces the time required to actually stretch and therefore tension the cable, and thus is well-suited for use with a flap-style anti-snag device shown in FIG. 3, because it enables the sliding platform to be moved towards the flap more quickly for a given amount of effort than is possible with previous devices.

Polymer surgical cables are frequently composed of materials having a remarkably low coefficient of friction such as polyethylene, thus it is a challenge to grasp them sufficiently for imparting tensile forces in excess of 100 lbs (~445N) as is required for surgical efficacy. The passive design of the present system is especially effective at reliably grasping such cables for such purposes. Testing in a simulated use environment, including simulation of lubricious physiological fluid contact, demonstrated that the present tensioning system is able to impart at least 900 Newtons of tensile load to a polymer surgical cable that is coated with physiological lubricant.

The embodiments of the invention described herein are exemplary and numerous modifications, variations and rearrangements can be readily envisioned to achieve substantially equivalent results, all of which are intended to be embraced within the spirit and scope of the invention as defined in the appended claims.

We claim:

1. A surgical cable tensioning system, comprising:
   a reaction frame;
   a sliding platform within said reaction frame, said platform arranged to move linearly within said frame along a first axis; and
   a clam-type cleat attached to said sliding platform, said clam-type cleat comprising:
   one or more grooves, each of which comprises two opposing arrays of ridges that converge to form a V-shape with said opposing arrays of ridges forming the inner walls of said groove, each of said one or more grooves having a longitudinal axis which is approximately parallel to said first axis and adapted to receive a length of cable such that said received length of cable lies along an axis approximately parallel to said groove's longitudinal axis, wherein the V-shape has a bottom at a juncture of the opposing arrays of ridges,
   the ridges of each groove being obliquely tilted relative to an axis perpendicular to said groove's longitudinal axis such that said length of cable is progressively captured between the ridges of said opposing arrays as the cable settles toward the bottom of said groove when moved in a first direction relative to said cleat, and such that said length of cable is disengaged from said cleat by relaxing the axial force on the length of cable and moving the length of cable in the direction opposite said first direction.

2. The system of claim 1, wherein said cleat comprises two of said grooves.

3. The system of claim 1, further comprising a linear actuator mechanism coupled to said sliding platform and arranged to move said sliding platform with respect to said reaction frame when actuated.

4. The system of claim 3, wherein said linear actuator mechanism is driven by manual or powered means.

5. The system of claim 3, wherein said linear actuator mechanism comprises a screw which moves said sliding platform with respect to said reaction frame when rotated.

6. The system of claim 5, wherein said screw is a multiple-start threaded screw.

7. The system of claim 1, wherein said cable is polymer surgical cable.

8. The system of claim 1, wherein the angle formed by the arrays of opposing ridges is wider near the opening of each groove than it is near the bottom of each groove.

9. The system of claim 1, wherein each of said grooves is arranged such that cables having a range of diameters can be captured by said groove without adjustment.

10. The system of claim 1, wherein the angle formed by the arrays of opposing ridges near the bottom of each groove is ≦25°.

11. The system of claim 1, wherein the angle with which the ridges of each groove are tilted relative to an axis perpendicular to said groove's longitudinal axis is 45±20°.

12. The system of claim 1, wherein the distance between the arrays of opposing ridges is adjustable.

13. The system of claim 1, further comprising an anti-snag device arranged to occlude said grooves and thereby prevent said length of cable from being captured.

14. The system of claim 13, wherein said anti-snag device is attached to said sliding platform and arranged such that it can be manually deployed to occlude said grooves.

15. The system of claim 1, further comprising a threading assist device coupled to said reaction frame, said threading assist device comprising:
at least one channel, each channel having a longitudinal axis which is approximately parallel to said first axis and adapted to receive a length of cable; and
upper and lower bars which span said channels so as to, in concert with the sidewalls of said channels, form at least one closed loop through which a length of cable to be tensioned is threaded enroute to the grooves of said cleat.

16. The system of claim 1, further comprising a cable retaining device through which a length of cable to be tensioned is threaded and which can be operated so as to inhibit movement of a length of cable so threaded with respect to said cable retaining device.

17. The system of claim 16, further comprising a threading assist device coupled to said reaction frame, said threading assist device comprising:
at least one channel, each channel having a longitudinal axis which is approximately parallel to said first axis and adapted to receive a length of cable; and
upper and lower bars which span said channels so as to, in concert with the sidewalls of said channels, form at least one closed loop through which a length of cable to be tensioned is threaded enroute to the grooves of said cleat;

wherein said threading assist device includes features arranged to engage with corresponding features on said cable retaining device so as to facilitate a desired alignment between said devices.

18. A surgical cable tensioning system, comprising:
a reaction frame;
a sliding platform within said reaction frame, said platform arranged to move linearly within said frame along a first axis; and
a clam-type cleat attached to said sliding platform, said clam-type cleat comprising:
one or more grooves, each of which comprises two opposing arrays of ridges that converge to form a V-shape with said opposing arrays of ridges forming the inner walls of said groove, each of said one or more grooves having a longitudinal axis which is approximately parallel to said first axis and adapted to receive a length of cable such that said received length of cable lies along an axis approximately parallel to said groove's longitudinal axis, wherein the V-shape has a bottom at a juncture of the opposing arrays of ridges,
the ridges of each groove being obliquely tilted relative to an axis perpendicular to said groove's longitudinal axis such that said length of cable is progressively captured between the ridges of said opposing arrays as the cable settles toward the bottom of said groove when moved in a first direction relative to said cleat, and such that said length of cable is disengaged from said cleat by relaxing the axial force on the length of cable and moving the length of cable in the direction opposite said first direction;
a linear actuator mechanism coupled to said sliding platform and arranged to move said sliding platform with respect to said reaction frame when actuated, said linear actuator mechanism comprising a screw which moves said sliding platform with respect to said reaction frame when rotated; and
a tightening knob which includes a torsion spring coupled to said screw such that turning the knob deflects the spring and adjusts the tension realized in a cable captured by said clam-type cleat.

19. A surgical cable tensioning system, comprising:
a reaction frame;
a sliding platform within said reaction frame, said platform arranged to move linearly within said frame along a first axis; and
a clam-type cleat attached to said sliding platform, said clam-type cleat comprising:
one or more grooves, each of which comprises two opposing arrays of ridges that converge to form a V-shape with said opposing arrays of ridges forming the inner walls of said groove, each of said one or more grooves having a longitudinal axis which is approximately parallel to said first axis and adapted to receive a length of cable such that said received length of cable lies along an axis approximately parallel to said groove's longitudinal axis, wherein the V-shape has a bottom at a juncture of the opposing arrays of ridges,
the ridges of each groove being obliquely tilted relative to an axis perpendicular to said groove's longitudinal axis such that said length of cable is progressively captured between the ridges of said opposing arrays as the cable settles toward the bottom of said groove when moved in a first direction relative to said cleat, and such that said length of cable is disengaged from said cleat by relaxing the axial force on the length of cable and moving the length of cable in the direction opposite said first direction; and an anti-snag device arranged to occlude said grooves and thereby prevent said length of cable from being captured, wherein said anti-snag device is attached to said reaction frame and is arranged such that it occludes said grooves when said clam-type cleat is at a predetermined position with respect to said frame.

20. A surgical cable tensioning system, comprising:

a reaction frame;

a sliding platform within said reaction frame, said platform arranged to move linearly within said frame along a first axis; and a clam-type cleat attached to said sliding platform, said clam-type cleat comprising:

one or more grooves, each of which comprises two opposing arrays of ridges that converge to form a V-shape with said opposing arrays of ridges forming the inner walls of said groove, each of said one or more grooves having a longitudinal axis which is approximately parallel to said first axis and adapted to receive a length of cable such that said received length of cable lies along an axis approximately parallel to said groove's longitudinal axis, wherein the V-shape has a bottom at a juncture of the opposing arrays of ridges, the ridges of each groove being obliquely tilted relative to an axis perpendicular to said groove's longitudinal axis such that said length of cable is progressively captured between the ridges of said opposing arrays as the cable settles toward the bottom of said groove when moved in a first direction relative to said cleat, and such that said length of cable is disengaged from said cleat by relaxing the axial force on the length of cable and moving the length of cable in the direction opposite said first direction; and a threading assist device coupled to said reaction frame, said threading assist device comprising:

at least one channel, each channel having a longitudinal axis which is approximately parallel to said first axis and adapted to receive a length of cable; and upper and lower bars which span said channels so as to, in concert with the sidewalls of said channels, form at least one closed loop through which a length of cable to be tensioned is threaded enroute to the grooves of said cleat, wherein said upper and lower bars are staggered along the longitudinal axis of said channels so as to increase the effective size of said closed loops.

21. A surgical cable tensioning system, comprising:

a reaction frame;

a sliding platform within said reaction frame, said platform arranged to move linearly within said frame along a first axis; and a clam-type cleat attached to said sliding platform, said clam-type cleat comprising:

one or more grooves, each of which comprises two opposing arrays of ridges that converge to form a V-shape with said opposing arrays of ridges forming the inner walls of said groove, each of said one or more grooves having a longitudinal axis which is approximately parallel to said first axis and adapted to receive a length of cable such that said received length of cable lies along an axis approximately parallel to said groove's longitudinal axis, wherein the V-shape has a bottom at a juncture of the opposing arrays of ridges, the ridges of each groove being obliquely tilted relative to an axis perpendicular to said groove's longitudinal axis such that said length of cable is progressively captured between the ridges of said opposing arrays as the cable settles toward the bottom of said groove when moved in a first direction relative to said cleat, and such that said length of cable is disengaged from said cleat by relaxing the axial force on the length of cable and moving the length of cable in the direction opposite said first direction;

a linear actuator mechanism coupled to said sliding platform and arranged to move said sliding platform with respect to said reaction frame when actuated; and a threading assist device coupled to said reaction frame, said threading assist device comprising:

two channels, each of which has a longitudinal axis which is approximately parallel to said first axis and adapted to receive a cable; and upper and lower bars which span said channels so as to, in concert with the sidewalls of said channels, form two closed loops through which two lengths of cable to be tensioned are threaded enroute to the grooves of said cleat.

22. A surgical cable tensioning system, comprising:

a reaction frame;

a sliding platform within said reaction frame, said platform arranged to move linearly within said frame along a first axis; and a clam-type cleat attached to said sliding platform, said clam-type cleat comprising:

one or more grooves, each of which comprises two opposing arrays of ridges that converge to form a V-shape with said opposing arrays of ridges forming the inner walls of said groove, each of said one or more grooves having a longitudinal axis which is approximately parallel to said first axis and adapted to receive a length of cable such that said received length of cable lies along an axis approximately parallel to said groove's longitudinal axis, wherein the V-shape has a bottom at a juncture of the opposing arrays of ridges, the ridges of each groove being obliquely tilted relative to an axis perpendicular to said groove's longitudinal axis such that said length of cable is progressively captured between the ridges of said opposing arrays as the cable settles toward the bottom of said groove when moved in a first direction relative to said cleat, and such that said length of cable is disengaged from said cleat by relaxing the axial force on the length of cable and moving the length of cable in the direction opposite said first direction;

a linear actuator mechanism coupled to said sliding platform and arranged to move said sliding platform with respect to said reaction frame when actuated;

a threading assist device coupled to said reaction frame, said threading assist device comprising:

two channels, each of which has a longitudinal axis which is approximately parallel to said first axis and adapted to receive a cable; and upper and lower bars which span said channels so as to, in concert with the sidewalls of said channels, form two closed loops through which two lengths of cable to be tensioned are threaded enroute to the grooves of said cleat; and a cable retaining device through which two lengths of cable to be tensioned are threaded and which can be operated so as to inhibit movement of the lengths of cable so threaded with respect to said cable retaining device.

* * * * *